United States Patent [19]

Fodor et al.

[11] Patent Number: 4,725,617

[45] Date of Patent: Feb. 16, 1988

[54] ALKYLAMINO-FURANON-DERIVATIVES

[75] Inventors: Tamas Fodor; Laszlo Dobay; Janos Fischer; Bela Stefko, all of Budapest; Bela Kiss, Vecses; Zsolt Szombathelyi; Egon Karpati, both of Budapest; Istvan Laszlovszky; Laszlo Szporny, both of Budapest, all of Hungary

[73] Assignee: Richter Gedeon Vegyeszeti Gyar R.T., Budapest, Hungary

[21] Appl. No.: 828,011

[22] Filed: Feb. 10, 1986

[30] Foreign Application Priority Data

Feb. 11, 1985 [HU] Hungary ................ 504/85

[51] Int. Cl.$^4$ ............... A61K 31/395; C07D 207/09
[52] U.S. Cl. ............... 514/422; 548/517; 548/533
[58] Field of Search .............. 548/517, 533; 514/422

[56] References Cited

U.S. PATENT DOCUMENTS 4,296,110 10/1981 Johnson .................. 548/533 X
4,431,644 2/1984 Smith et al. ............. 548/533 X

OTHER PUBLICATIONS

Noller, "Chemistry of Organic Compounds", 3rd ed. (1965), pp. 236–237, 858–859; W. B. Saunders Co. Philadelpia.

Weygand/Hilgetag, "Preparative Organic Chemistry", (1972), p. 404; John Wiley & Sons, New York.

Primary Examiner—Joseph Paul Brust
Attorney, Agent, or Firm—Karl F. Ross; Herbert Dubno; Jonathan Myers

[57] ABSTRACT

The present invention relates to a compound of the formula (I)

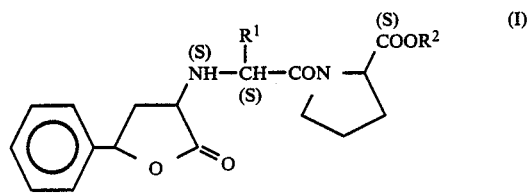

wherein

R$^1$ stands for methyl or a group of the formula R$^3$—NH—(CH$_2$)$_4$—wherein R$^3$ is hydrogen or a protective group being compatible with the peptide bond, R$^2$ represents hydrogen, a protective group being compatible with the peptide bond or a cation derived from an organic or inorganic base the pharmaceutically acceptable salts and diastereomers thereof.

The compounds of the invention are useful for inhibiting the effect of the angiotensin converting ensime and they can be used in the therapy as blood pressure reducing agents and for the treatment of cardiac failure and glaucoma.

5 Claims, No Drawings

ALKYLAMINO-FURANON-DERIVATIVES

TECHNICAL FIELD

The present invention relates to novel alkylamino-furanon derivatives of the formula (I)

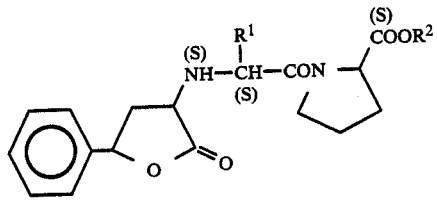

the pharmaceutically acceptable salts and diastereomers thereof, a process for preparing the same, pharmaceutical formulations comprising the same and a method for reducing the blood pressure and treating cardiac failure and glaucoma by these compounds.

SUMMARY OF THE INVENTION

In the above formula (I)
$R^1$ stands for methyl or a group of the formule $R^3$-NH-$(CH_2)_4$-, wherein
  $R^3$ is hydrogen or a protective group being compatible with the peptide bond,
  $R^2$ is hydrogen, a protective group being compatible with the peptide bond or a cation derived from an organic or inorganic base.

Suitable amino-protecting groups are described in several textbooks, e.g. by Houben-Weyl [Die Methoden der Organischen Chemie, 15 (1), G. Thieme Verlag, Stuttgart (1974), pp. 46–305], and protective groups for the carboxylic group are also well known [ibid., 15 (1), pp. 315–447].

The N-terminal group of the compounds of the formula (I) can form salts with inorganic or organic acids. If $R^2$ stands for hydrogen, then the free C-terminal carboxyl can form salts with inorganic or organic bases or a salt of twin ion character.

Suitable pharmaceutically acceptable salts of the carboxy group of the compound of the formula (I) include e.g. alkali metal salts such as sodium or potassium, alkaline earth metal salts such as calcium or magnesium and ammonium or substituted ammonium salts, for example those with lower alkylamines such as triethylamine, hydroxy-lower alkyl-amines such as 2-hydroxyethylamine, cycloalkylamines such as dicyclohexylamine.

Suitable acids for forming pharmaceutically acceptable salts on the N-terminal group are e.g. hydrochloric, hydrobromic, sulfuric, phosphoric acid, $C_{1-6}$ mono- or dicarboxylic acids, e.g. formic acid, acetic acid, maleinic acid, tartaric acid etc. Hydrochloric acid and maleinic acid are the most preferred.

Of the compounds of the formula (I) the most preferred one is N-[5-(R,S)-phenyl-dihydro-2(3H)-furanon-3(S)-yl]-(S)-alanyl-(S)-proline, the diastereomers and the pharmaceutically acceptable salts thereof. The effect of this compound was examined on rats suffering from spontaneous hypertonia. The effect of this compound is about the same as that of enalapril [N-[1(S)-etoxycarbonyl-3-phenylpropyl]-(S)-alanyl-(S)-proline, disclosed in European patent specification No. 12,401] in a dose of 2 mg/kg p.o., however, the effect can be sooner observed and the period of its activity is remarkably longer.

The amino acids being in the dipeptic portion of the Formula (I) and position 3 of the furane ring are of (S)-configuration; the position 5 of the furane ring is chiral and it may be of (S) or (R) configuration, thus the configuration of the compounds of the formula (I) may be R,S,S,S or S,S,S,S. If the diastereomers are not separated, then the compounds of the formula (I) comprise a mixture of the two diastereomers.

In the course of our experiments it was found that the compounds of the Formula (I) can be simply prepared by cyclizing the gama-hydroxy-carboxylic esters of the formula (II)

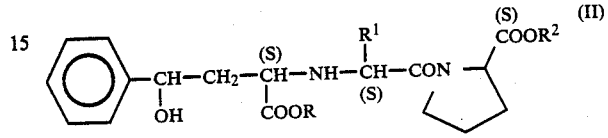

or the salts thereof, If the formula (II) the definition of $R^2$ and $R^1$ is the same as given hereinabove, R stands for hydrogen or alkyl having 1 to 4 carbon atoms.

When the activity of the compounds according to the present invention was examined, it was found that primarily they inhibit the effect of the angiotensin converting enzyme and they can be used in the therapy as blood pressure reducing agents and for the treatment of cardiac failure and glaucoma.

DETAILED DESCRIPTION OF THE INVENTION

According to the present invention the compounds of the formula (I) are prepared by cyclizing a novel compound of the formula (II) or the salt thereof in the presence of an acid, and (a) optionally separating the compound of the formula (I) optionally formed in the form of a salt into diastereomers, thereafter optionally removing the protecting groups(s) $R^2$ and/or $R^3$, and if desired transforming the diastereomers wherein $R^2$ and $R^3$ both hydrogen into (other) pharmaceutically acceptable salts optionally after liberation from their salts, or (b) removing the protective groups $R^2$ and/or $R^3$ from the compound of the formula (I) optionally formed as a salt, optionally separating the compound of the formula (I), wherein $R^2$ and $R^3$ stand for hydrogen into two diastereomers, thereafter isolating the diastereomers in the form of a base or a pharmaceutically acceptable salt.

According to the process of the invention a novel compound of the formula (II) or a salt thereof is used as starting material. The novel compounds of the formula (II) may be prepared e.g. by carrying out a Michael reaction with compounds of the formulae (V) and (IV)

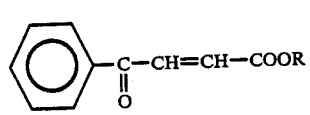

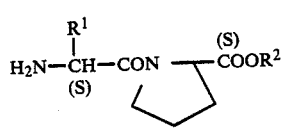

then reducing the compound of the formula (III)

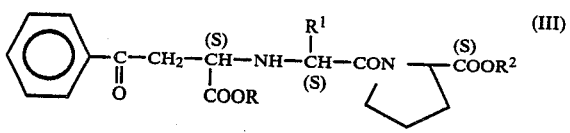

thus obtained. In the formulae (III), (IV) and (V) the meaning of the substituents is the same as defined hereinabove. The reduction of the compound of the formula (III) can be carried out by catalytic hydrogenation, or the acid addition salt of the compound of the formula (III) may be reduced by e.g. a borohydride. The preparation of the compound of the formula (II) used as starting material is described in the examples in details.

In the compound of the formula (II) used as starting material the chiral carbon atoms are of S-configuration in all the three amino acid portions, the steric arrangement of the hydroxyl group may be of R or S configuration. Thus the compounds of the formula (II) are a mixture of diastereomers of the configurations R,S,S,S and S,S,S,S which can be separated when it is desired. When the compound of the formula (II) of R,S,S,S configuration is used as starting material, a compound of the formula (I) of R,S,S,S configuration is formed, while when a compound of the formula (II) of S,S,S,S configuration is employed, a compound of the formula (I) of S,S,S,S configuration is obtained. If the diastereomers of the formula (II) are not separated, then a mixture of the diastereomers of the compound of the formula (I) is obtained after cyclizing, where the desired diastereomer can subsequently be separated from.

According to the process of the invention the compound of the formula (II) or a salt thereof is cycled in the presence of a suitable acid. The reaction is carried out at a temperature of 20° to 100° C.

If a compound of the formula (II) wherein $R^2$ and $R^3$ stand for protective groups being compatible with the peptide bond and a weak acid (e.g. glacial acetic acid) are used, then the protective groups are not cleaved in the course of the cycling reaction, they can be removed in a separate step from the compound of the formula (II). If the cyclisation is carried out in the presence of a strong acid (e.g. trifluoroacetic acid), then the acid-sensitive protective groups (e.g. t-butyl group) are cleaved in the course of the cycling reaction, i.e. a compound of the formula (I) wherein $R^2$ and $R^3$ are both hydrogen is obtained.

If a mixture of the diastereomers of the compound of the formula (II) is used as starting material, then it depends on the reaction medium whether the compound of the formula (I) thus obtained is a mixture of diastereomers or only one diastereomer is formed.

If the mixture of the diastereomers of the compound of the formula (II) is cycled in a weak acid (e.g. glacial acetic acid) or a strong acid (e.g. trifluoroacetic acid), then a diastereomer mixture is obtained, which can be separated on the basis of the difference between the solubility of the components or by chromatography.

If the mixture of the diastereomers of the compound of the formula (II) is cyclized in a mixture of a weak acid (e.g. silica gel or glacial acetic acid) and an inert solvent (e.g. acetone), then only the compound of the formula (II) of the R,S,S,S configuration is cycled to the corresponding compound of the formula (I) of R,S,S,S configuration, while the diastereomer of the compound of the formula (II) of the S,S,S,S configuration will remain unchanged. Thus in the mixture of a weak acid and an inert solvent the reaction is diastereomer-selective.

If the salt of the compound of the formula (II) formed with a strong acid is cyclized, then the compound of the formula (I) may be isolated in the form of the same salt. If another salt is desired to be prepared, then the compounds of the formula (I) thus obtained are liberated from their salts by the aid of organic or inorganic bases, or if $R^2$ stands for hydrogen, then the pH is adjusted to the isoelectric point in an inert solution by the aid of an organic or inorganic base, then the salt is precipitated from the isolated compound of the formula (I) in a manner known per se.

The process according to the invention and the preparation of the novel starting materials are illustrated by the following, non-limiting examples.

EXAMPLE 1

Preparation of the 5(R) and 5(S) diastreomers of N-[5-phenyl-dihydro-2(3H)-furanone-3-(S)]-yl-(S)-alanyl-(S)-proline-t.-butylester hydrochloride 13.4 g (30 mmoles) of N-[1-(S)-ethoxycarbonyl-3-phenyl-3-oxo-propyl]-(S)-alanyl-(S)-proline-t - butylester are dissolved in 120 ml of ethanol and hydrogenated in the presence of 1.5 g of 10% palladium-on-charcoal catalyst at room temperature. After the uptake of the theoretically needed hydrogen (720 ml), the catalyst is filtered off. A mixture of N-[1-(S)-ethoxycarbonyl-3-phenyl-3(S)-hydroxypropyl]-(S)-alanyl-(S)-proline-t-butylester and N-[1-(S)-ethoxycarbonyl-3-phenyl-3(R)-hydroxypropyl]-(S)-alanyl-(S)-proline-t-butylester is obtained.

To the filtrate comprising the mixture of the diastereomers 10 ml of 3N hydrochloric ethanol are added, then the solvent is evaporated off. The components of the diastereomer mixture being in the form of a hydrochloride salt can be identified by thin-layer chromatography. (Adsorbent: Kieselgel 60 $F_{254}$; eluent: a 70:10:30 mixture of ethylacetate/glacial acetic acid/diisopropylether.) $R_f$(S,S,S,S): 0.09. $R_f$(R,S,S,S): 0.15.

The substance obtained after the evaporation of the solvent is dissolved in 100 ml of glacial acetic acid and stirred at a temperature of 50° to 60° C. for 24 hours. The glacial acetic acid is evaporated off under reduced pressure, the residue is treated with 150 ml of ethyl acetate. The precipitated crystalline substance is filtered, washed with ethyl acetate and recrystallized from acetonitrile. 4.65 g of N-[5(R)-phenyl-dihydro-2(3H)-furanone-3-(S)-yl]-(S)-alanyl-(S)-proline-t-butylester hydrochloride are obtained. Yield: 35.2%.

Melting point: 210°–211° C. (dec.).

$R_f$:0.36

$[\alpha]_D^{25} = -72.3°$ (c=1, methanol).

The mother liquor obtained in the crystallization step is concentrated, the precipitated crystalline substance is filtered and washed with acetone. 4.2 g of solid N-[5(S)-phenyl-dihydro-2(3H)-furanone-3(S)-yl]-(S)-alanyl-(S)-proline-t-butylester hydrochloride are obtained. After recrystallization from methyl ethyl ketone 3.55 g of product can be achieved (25.5%), M.p.: 183°–185° C. (dec.)

$R_f$:0.54.

$[\alpha]_D^{25} = -106.43°$ (c=1, methanol).

Total yield: 60.7%.

EXAMPLE 2

N-[5(S)-phenyl-dihydro-2(3H)-furanone-3(S)-yl]-(S)-alanyl-(S)-proline maleate 0.44 g (1 mmole) of N-[5(S)-phenyl-dihydro-2(3H)-furanone-3(S)-yl]-[S]-alanyl-[S]-proline-t-butylester hydrochloride prepared according to Example 1 are dissolved in 2 ml of 6N hydrochloric diaxane and stired for 2 hours at room temperature. The hydrochloric dioxane is evaporated off under reduced pressure, the residue is dissolved in 10 ml of dichloromethane and the pH is adjusted to 4.2 by adding 8% aqueous sodium carbonate solution. The phases are separated, the aqueous phase is washed with 2×5 ml of dichloromethane. The combine dichloromethane solution is washed with 10 ml of saturated sodium chloride solution, and dried over anhydrous magnesium sulphate. The dichloromethane is evaporated off after filtering the drying agent. The residue is dissolved in 3 ml of acetonitride and the maleinic salt is prepared by adding 0.11 g of maleinic acid. The precipitated product is cooled to a temperature of 0° C., filtered off after a 3 hours crystallization and washed with ether.

Yield: 0.43 g (93%)
Mp.: 121°-123° C.
$R_f=0.33$ (eluent: a 20:11:6:86 mixture of pyridine/glacial acetic acid/water/ethyl acetate)
$[\alpha]_D^{25} = -82.8°$ (c=1, methanol)

EXAMPLE 3

N-[5(R)-phenyl-dihydro-2(3H)-furanone-3(S)-yl]-(S)-alanyl-(S)-proline and the maleate salt thereof 0.44 g (1 mmole) of N-[5(R)-phenyl-dihydro-2(3H)-furanone-3(S)-yl]-(S)-alanyl-(S)-proline-t-butylester hydrochloride prepared according to Example 1 are dissolved in 2 ml of 6N hydrochloric dioxane and stirred at room temperature for 2 hours. The hydrochloric dioxane is evaporated off under reduced pressure, the residue is dissolved in 10 ml of dichloromethane, then the pH is adjusted to 4.2 by adding 8% aqueous sodium carbonate solution. The phases are separated, and the aqueous phase is washed with 2×5 ml of dichloromethane. The combined dichloromethane solutions are washed with 10 ml of saturated aqueous sodium chloride solution and dried over anhydrous magnesium sulphate. The solution substance obtained after evaporating off of the dichloromethane is recrystallized from methanol.

Yield: 0.31 g (91%).
$R_f=0.26$ (eluent: a 20:11:6:86 mixture of pyridine/glacial acetatic acid/water/ethyl acetate) 0.17 g (0.5 mmoles) of the product thus obtained are dissolved in 1.5 ml of acetonitrile and 0.058 g (0.5 mmoles) of maleinic acid are added. The crystalline substance thus obtained is stirred at 0° C. for 2 hours, filtered and dried.

Yield: 0.22 g (95%).
M.P.: 151°-153° C.
$[\alpha]_D^{25} = -46.63°$ (c=1, methanol)

EXAMPLE 4

N-[5(R,S)-phenyl-dihydro-2(3H)-furanone-3(S)-yl]-(S)-alanyl-(S)-proline 4.46 g (10 mmoles) of N-[1(S)-ethoxy-carbonyl-3-phenyl-3-oxo-propyl]-(S)-alanyl-(S)-proline-t-butylester are dissolved in 40 ml of ethanol and hydrogenated in the presence of 0.5 g of 10% palladium-on-charachoal at room temperature.

After the uptake of the theoretically necessary hydrogen (240 ml) the catalyst is filtered off and the ethanol is evaporated off under reduced pressure. The residue is dissolved in 20 ml of trifluoroacetic acid and stirred for 2 hours at room temperature. The trifluoroacetic acid is evaporated off, the residual white solid substance is dissolved in 20 ml of dichloromethane and the pH is adjusted to 4.2 by adding 8% aqueous sodium carbonate solution. The aqueous phase is washed with 2×10 ml of dichloromethane. The organic phase is washed with 10 ml of saturated sodium chloride solution, dried over anhydrous magnesium sulphate, filtered and the dichloromethane is evaporated off from the filtrate.

Yield: 3.05 g (89%) (the mixture of the diastereomers of the title product).
M.p.: 70°-90° C.
$R_f=0.26$ and 0.33.

EXAMPLE 5

N-[5(S)-phenyl-dihydro-2(3H)-furanone-3(S)-yl]-(S)-alanyl-(S)-proline maleate 4.83 g (10 mmoles) of N-[1(S)-etoxycarbonyl3-phenyl-3-oxo-propyl]-(S)-alanyl-(S)-proline-t-butylester hydrochloride are dissolved in 25 ml of ethanol and 0.8 g of sodium cyanoborohydride are added in small portions. The reaction mixture is stirred for 24 hours at room temperature, then filtered through celite after adding 0.7 ml of glacial acetic acid dropwise and the solvent is evaporated off from the filtrate under reduced pressure. 20 ml of 6N hydrochloric dioxane are added to the residue and the solution is stirred for 2 hours at room temperature. The solid substance obtained after the evaporation of the hydrochloric dioxane is dissolved in 30 ml of dichloromethane, and the pH is adjusted to 4.2 by adding 8% aqueous sodium carbonate solution. The phases are separated, the aqueous phase is saturated with sodium chloride and extracted with 2×10 ml of dichloromethane. The combined dichloromethane solutions are dried over anhydrous magnesium sulphate, filtered and the solvent is evaporated off from the filtrate. The residue is dissolved in 15 ml of acetonitrile and the maleinic salt is prepared by adding 1.16 g of maleinic acid. The precipitated crystalline substance is cooled to 0° C., filtered and washed with acetonitrile.

Yield: 1.98 g (43%) of the title product, which physical characteristics are the same as described in Example 2.

0.62 g (18%) of N-[5(R)-phenyl-dihydro-2(3H)-furanone-3(S)-yl]-(S)-alanyl-(S)-proline are isolated from the mother liquor, which physical characteristics are the same as described in Example 3.

EXAMPLE 6

Preparation of
N-[5(R)-phenyl-dihydro-2(3H)-furanone-3(S)-yl]-(S)-alanyl-(S)-proline-t-butylester hydrochloride (compound a) and
N-[5(S)-phenyl-dihydro-(3H)-furanone-3(S)-yl]-(S)-alanyl-(S)-proline-t-butylester hydrochloride (compound b)

10 g (20 mmoles) of N-[1(S)-ethoxycarbonyl-3-phenyl-3-3(R,S)-hydroxy-propyl]-(S)-alanyl-(S)-proline-t-butylester hydrochloride are dissolved in 60 ml of acetone. 15 ml of glacial acetic acid are added to the solution and it is refluxed for 8 hours, the solvent is evaporated off under reduced pressure and 20 ml of ethylacetate are added to the residue. The precipitated crystalline substance is filtered off.

Yield: 4.21 g (47%) of title compound a.
M.p.: 210°–211° C. (dec.)

The solvent is evaporated off from the mother liquor, 20 ml of glacial acetic acid are added to the residue and the solution is stirred at a temperature of 60° C. for 12 hours. The glacial acetic acid is evaporated off under reduced pressure, the residue is treated with a 4:1 mixture of ethyl acetate and diethyl ether in order to obtain a crystalline substance.

Yield: 3.31 g (37%) of title compound b.
M.p: 183°–185° C.

The total yield of compounds a and b are 84%.

EXAMPLE 7

N-[1(S)-ethoxycarbonyl-3-phenyl-3-oxo-propyl]-(S)-alanyl-(S)-proline-t-butyl-ester maleate 4.84 g (20 mmoles) of (S)-alanyl-(S)-proline-t-butylester are dissolved in 40 ml of dry benzene and 4.08 g (20 mmoles) of E-ethyl-3-benzoyl-acrylate are added at room temperature under stirring. After one hour stirring at room temperature the solvent is evaporated off under reduced pressure, the residue is dissolved in 20 ml of ethyl acetate and 2.32 g (20 mmoles) of maleinic acid are added. The precipitated crystals are filtered off after one hour standing and washed with 20 ml of ethyl acetate. 6.7 g (60%) of product are obtained with a melting point of 109°–110° C.

EXAMPLE 8

$N_\alpha$-[5(R)-phenyl-dihydro-2(3H)-furanone-3(S)-yl]-$N_\epsilon$-t-butoxycarbonyl-(S)-lysyl-(S)-proline-t-butylester hydrochloride 6.03 g (10 mmoles) of $N_\alpha$-[1(S)-ethoxy-carbonyl-3-phenyl-3-oxo-propyl]-$N_\epsilon$-t-butoxycarbonyl-(S)-lysyl-(S)-proline-t-butylester are dissolved in 80 ml of ethylacetate and 3.34 ml (10 mmoles) of 3N hydrochloric ethyl acetate and 0.6 g of 10% palladium--on-charcoal catalyst are added. The hydrogenation is carried out under ambient pressure at room temperature. After the uptake of 10 mmoles of hydrogen the catalyst is filtered off and the ethyl acetate is evaporated off. 6.28 g (98%) of $N_\alpha$-[1(S)ethoxycarbonyl-3-phenyl-3(S)-hydroxy-propyl]-$N_\epsilon$-t-butoxycarbonyl-(S)-lysyl-(S)-proline-t-butylester hydrochloride ($R_f$=0.31 in a 7:1:3 mixture of ethylacetate/glacial acetic acid/diisopropylether) and $N_\alpha$-[1(S)-ethoxycarbonyl-3-phenyl-3(R)-hydroxy-propyl]-$N_\epsilon$-t-butoxycarbonyl-(S)-lysyl-(S)-proline-t-butylester hydrochloride ($R_f$=0.35 in the same eluent mixture) are obtained. This mixture of diastereomers is dissolved in 100 ml of acetone supplemented with 1 ml of glacial acetic acid and the solution is refluxed for 10 hours. After evaporation of the solvent the residue is dissolved in 50 ml of diethyl ether and cooled to a temperature of 0° C. After 5 hours cooling the precipitated crystalline substance is filtered off and washed with cold ether.

Yield: 2.16 g (36.4%) of title compound.
M.p.: 114°–115° C.
$[\alpha]_D^{25}$ = −61.3° (c=1, methanol).
$R_f$=0.54 (in a 7:1:3 mixture of ethylacetate/glacial acetic acid/diisopropyl ether)

The other diastereomer, the $N_\alpha$-[5(S)-phenyl-dihydro-2(3H)-furanone-3(S)-yl]-$N_\epsilon$-t-butoxycarbonyl-(S)-lysyl-(S)-proline-t-butylester hydrochloride remained in the mother liquor. ($R_f$:0.60)

EXAMPLE 9

$N_\alpha$-[5(R)-phenyl-dihydro-2(3H)-furanone-3(S)-yl]-(S)-lysyl-(S)-proline dihydrochloride 0.6 g (1 mmole) of $N_\alpha$-[5(R)-phenyl-dihydro-2(3H)-furanone-3(S)-yl]-$N_\epsilon$-t-butoxycarbonyl-(S)-lysyl-(S)-proline-t-butylester hydrochloride are stirred with 5 ml of 6N hydrochloric dioxane at room temperature. After evaporation of the hydrochloric dioxane, the residue is suspended in diethyl ether, filtered off, washed with diethyl ether and petroleamether (boiling point: 40° C.) and dried in a desiccator over phosphorous pentoxide. 0.45 g (94 %) of product are obtained.

M.p: 176° C. (dec.)
$[\alpha]_D^{25}$ = −39.40° (c=1, methanol)
$R_f$=0.59 (in a 1:1:1:1 mixture of ethylacetate/n-butanol/glacial acetic acid/water) and 0.72 (in a 38:11:21:30 mixture of pyridine/glacial acetic acid/water/ethyl acetate)

EXAMPLE 10

$N_\alpha$-[5(R)-phenyl-dihydro-2(3H)-furanone-3(S)-yl]-(S)-lysyl-(S)-proline-dihydrochloride and
$N_\alpha$-[5(S)-phenyl-dihydro-2(3H)-furanone-3(S)-yl]-(S)-lysyl-(S)-proline dihydrochloride 6.03 g (10 mmoles) of $N_\alpha$-[1(S)-ethoxycarbonyl-3phenyl-3-oxo-propyl]-$N_\epsilon$-t-butoxycarbonyl-(S)-lysyl-(S)-proline-t-butylester are dissolved in 80 ml of ethyl acetate, thereafter 3.34 ml (10 mmoles) of 3N hydrochloric ethyl acetate and 0.6 g of 10% palladium-on-characoal catalyst are added. The hydrogenation is carried out at room temperature under ambient pressure. After the uptake of 10 mmoles of hydrogen the catalyst is filtered off and the ethyl acetate is evaporated. 6.28 g (98%) of $N_\alpha$-[1(S)-ethoxycarbonyl-3-phenyl-3(S)-hydroxy-propyl]-$N_\epsilon$-t-butoxy-carbonyl-(S)-lysyl-(S)-proline-t-butylester hydrochloride ($R_f$=0.31 in a 7:1:3 mixture of ethyl acetate/glacial acetic acid/diisopropyl ether) and $N_\alpha$-[1(S)-ethoxycarbonyl-3-phenyl-3(R)-hydroxy-propyl]-$N_\epsilon$-t-butoxycarbonyl-(S)-lysyl-(S)-proline-t-butylester dihydrochloride ($R_f$=0.35 in the same eluent) are obtained. This diastereomer mixture is dissolved in 20 ml of 6N hydrochloric dioxane and the solution is stirred for 2 hours at room temperature. The hydrochloric dioxane is evaporated off, the residue is suspended in ethyl acetate, filtered and washed with diethyl ether and petrolether (boiling point: 40° C.) and dried in a desiccator over phosphorus pentoxide. 4.04 g (85%) of product are obtained.

$R_f$(S,S,S,S): 0.65 (hydrochloric salt)

R$_f$ (R,S,S,S): 0.59 (hydrochloric salt) (Eluent: a 1:1:1:1 mixture of ethyacetate/n-butanol/glacial acetic acid/water)

The preparation of the starting material used in Example 8 is illustrated by Example 11.

EXAMPLE 11

N$_\alpha$-[1(S)-ethoxycarbonyl-3-phenyl-3-oxo-propyl]-N$_\epsilon$-t-butoxycarbonyl-(S)-lysyl-(S)-proline-t-butylester 8.0 g (20 mmoles) of N$_\epsilon$-t-butoxycarbonyl-(S)-lysyl-(S)-proline-t-butylester are dissolved in 100 ml of diethyl ether and 4.48 g (22 mmoles) of E-ethyl-3-benzoyl-acrylate are added to the solution. The reaction mixture is stirred at room temperature for 5 hours. After evaporation of the solvent the title product is isolated on a Kieselgel column in the form of transparent oil. R$_f$=0.49 i(in a 7:3 eluent mixture of ethyl acetate and ether).

DOSAGE FORMS

The active agents of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be adminixtered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration: age, health, and weight of the recipient; nature and extent of symptons, kind of concurrent treatment, frequency of treatment and the effect desired. Usually a daily dosage of active ingredient can be about 0.5-10 milligrams per kilogram of body weight. Ordinarily, when the more potent compounts of this invention are used, 1-5, and preferably 1-3 milligrams per kilogram per day, given preferably in a single dose is effective to obtain desired results.

Dosage forms (compositions) suitable for internal administration contain from about 1.0 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

In generaly, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidants wuch as sodium bisulfate, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Sutiable pharmaceutical carriers are described in *Remington's Pharmaceutical Sciences*. A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 50 milligrams of powdered active ingredient, 150 milligrams of lactose, 24 milligrams of talc and 6 milligrams of magnesium stearate.

SOFT GELATIN CAPSULES

A mixture of active ingredient in soybean oil is prepared and injected by means of a positive displacement pump into gelatin to form soft gelatin capsules containing 20 milligrams of the active ingredient. The capsules are washed and dried.

TABLETS

A large number of tablets are prepared by conventional procedures so that the dosage unit is 75 milligrams of active ingredient, 0.2 milligrams of colloidal silicon dioxide, 5 milligrams of magnesium stearate, 250 milligrams of microcrystalline cellulose, 11 milligrams of cornstarch and 98.8 milligrams of lactose. Appropriate coatings may be applied to increase palatability or delay absorption.

We claim:

1. An alkylamino-furanon of the formula (I)

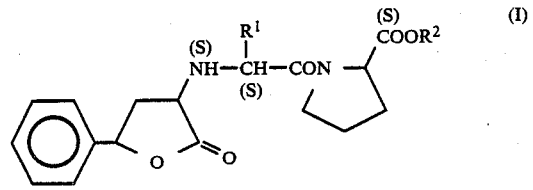

wherein
R$^1$ stands for methyl or a group of the formula R$^3$-NH-(CH$_2$)$_4$ -wherein R$^3$ is hydrogen or t-butoxycarbonyl,
R$^2$ represents hydrogen, t-butyl or an alkali metal, alkaline earth metal or ammonium cation derived from a pharmaceutically acceptable organic or inorganic base, or a pharmaceutically acceptable acid addition salt or diastereomer thereof.

2. A hypotensive pharmaceutical composition which comprises a hypotensively effective amount of a compound of the formula (I) as defined in claim 1, a diastereomer or a pharmacutically acceptable acid addition salt thereof in association with a suitable inert carrier diluent or excipient.

3. A method for reducing the blood pressure or treating cardiac failure or glaucoma in mammals which comprises administering to a subject a hypotensively effective amount of the compound of the formula (I) as defined in claim 1, or a diastereomer or pharmaceutically acceptable acid addition salt thereof.

4. The compound of the Formula (I) defined in claim 1 selected from the group consisting of N-[5(R,S)-phenyl-dihydro-2(3H)-furanone-3(S)-yl]-(S)-alanyl-(S)-proline and N-[5(R,S)-henyl-dihydro-2(3H)-furanone-3(S)-yl]-(S)-lysyl-(S)-proline, or a pharmaceutycally acceptable acid addition salt or diastereomer thereof.

5. A compound of the formula (II)

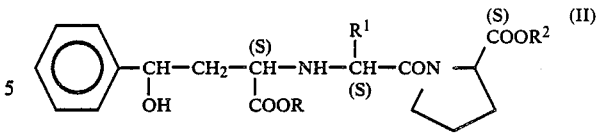

wherein
R stands for hydrogen or alkyl having 1 to 4 carbon atoms,
$R^1$ stands for methyl or a group of the formula $R^3$-NH-$(CH_2)_4$- wherein $R^3$ is hydrogen or t-butoxy carbonyl,
$R^2$ represents hydrogen, t-butyl or an alkali metal, alkaline earth metal or ammonium cation derived from a pharmaceutical acceptable organic or inorganic base, or a
diastereomer or pharmaceutically acceptable acid addition salt thereof.

* * * * *